United States Patent [19]

Kligman et al.

[11] 4,318,907

[45] Mar. 9, 1982

[54] METHOD FOR TREATING ACNE VULGARIS AND COMPOSITIONS USEFUL FOR THAT PURPOSE

[75] Inventors: Albert M. Kligman, Philadelphia, Pa.; Walter L. McKenzie, Williamsville; Peter F. Ciesla, Lancaster, both of N.Y.

[73] Assignee: Westwood Pharmaceuticals, Inc., Buffalo, N.Y.

[21] Appl. No.: 893,239

[22] Filed: Apr. 4, 1978

[51] Int. Cl.³ .................... A61K 31/075; A61K 31/60
[52] U.S. Cl. ...................................... 424/230; 424/338
[58] Field of Search ......................... 424/338, 230, 235

[56] References Cited

U.S. PATENT DOCUMENTS

| 2,095,571 | 10/1937 | Nichols | 424/235 |
|---|---|---|---|
| 2,523,867 | 9/1950 | Donnelly | 424/234 |
| 2,614,962 | 10/1952 | Olson | 424/184 |
| 3,265,571 | 8/1966 | Kreznoski | 424/235 |
| 3,343,540 | 9/1967 | Siegel | 128/269 |
| 3,530,217 | 9/1970 | White et al. | 424/180 |
| 3,535,422 | 10/1970 | Cox et al. | 424/164 |
| 3,821,370 | 6/1974 | Tenta | 424/145 |
| 3,949,072 | 4/1976 | Tenta | 424/145 |
| 3,987,202 | 10/1976 | Okun | 424/331 |

FOREIGN PATENT DOCUMENTS

| 645930 | 9/1964 | Belgium . |
| 2340568 | 2/1974 | Fed. Rep. of Germany . |
| 2416542 | 4/1974 | Fed. Rep. of Germany . |
| 964444 | 7/1964 | United Kingdom . |
| 1185685 | 3/1970 | United Kingdom . |

OTHER PUBLICATIONS

Stiefel Laboratory Brochure, "The Better Acne Therapy Panoxyl Acne Gel", 10-1977.

*Primary Examiner*—Leonard Schenkman
*Attorney, Agent, or Firm*—Morton S. Simon

[57] ABSTRACT

Procedure for treating acne vulgaris that uses salicylic acid and benzoyl peroxide either sequentially or simultaneously. Compositions for practicing each of these aspects of the invention are also described.

13 Claims, No Drawings

METHOD FOR TREATING ACNE VULGARIS AND COMPOSITIONS USEFUL FOR THAT PURPOSE

This invention relates to procedures for treating acne vulgaris that employ salicylic acid and benzoyl peroxide as active ingredients. It also concerns topical therapeutic compositions that are useful for this purpose and particularly stable compositions of this character.

The pathology of acne vulgaris is believed to involve a number of factors; the first of which is the formation of comedones more commonly referred to as whiteheads (closed comedones) and blackheads (open comedones). These are solid horny masses that plug follicles and are associated with increased production of sebum. They are made up of tightly packed keratinized cells. These plugs are white (whiteheads) when originally formed but through continued growth and deposition of the normal pigment, pigment melanin becomes blackheads.

As the comedo enlarges through continued accumulation of keratinized cells, pressure builds up within the follicles which eventually rupture, dumping the contents consisting of horny material, sebum and bacteria into the skin. This provokes inflammatory responses which take the form of pustules (pimples) when the rupture is small and cystic-nodules with complete rupture.

One of the prior art modes for the treatment of acne vulgaris has been the application of a keratolytic agent for the purpose of drying and peeling the skin to remove the keratinous plugs. The agents used for this purpose include sulfur, resorcinol, resorcinol monoacetate and salicylic acid. Hexachlorophene has also frequently been added for its antibacterial effect. (See "Handbook of Non-Prescription Drugs", 1969 Edition pages 118-121, published by the American Pharmaceutical Association, Washington, D.C.). U.S. Pat. No. 3,530,217 also suggests that other antibacterial agents such as parachlorometaxylenol, tyrothricin, neomycin sulfate, benzalkonium chloride and Bithinonol may be used along with keratolytic agents such as sulfur, resorcinol, salicylic acid and benzoyl peroxide in the treatment of acne.

It has now been found that benzoyl peroxide and salicylic acid when used together at certain specified levels, exhibit a therapeutic effect greater than either agent alone in treating acne. These materials may be used in combination with each other in the treatment of acne or may be employed in a regimen of treatment in which one is applied after the other.

It is accordingly an object of this invention to provide procedures for the treatment of acne vulgaris that involve the use of salicylic acid and benzoyl peroxide at certain specified levels simultaneously (e.g. with both active ingredients in the same vehicle) or sequentially (e.g. with the active ingredients in separate vehicles).

It is also an object of this invention to provide compositions or articles of manufacture carrying salicylic acid and benzoyl peroxide at certain specified levels that are especially useful in the treatment of acne vulgaris.

It is still a further object of this invention to provide gel compositions which are chemically and physically stable (i.e. exhibit no degradation of active components or deterioration of the gel system) containing salicylic acid and benzoyl peroxide at certain specified levels that are useful in the treatment of acne vulgaris.

Other and more detailed objects of this invention will be apparent from the following description and claims.

Benzoyl peroxide is antimicrobial and suppresses the acne bacillus, *Propionibacterium acnes,* an organism which has an important casual role in acne vulgaris. Salicylic acid, on the other hand, is not just another keratolytic agent like resorcinol, phenol and other traditional agents which have been used to cause peeling. It belongs to a special class of comedolytic drugs which interfere with the formation of blackheads and whiteheads, horny masses which clog the follicles. Few keratolytic agents have this property, the other well-known one being vitamin A acid. Above and beyond the comedolytic effect, salicylic acid has other properties which add uniqueness to the present combination. It weakens the horny layer barrier, thereby increasing the permeability of skin to the benzoyl peroxide. As a result of its effect on the barrier, the tissue concentration of benzoyl peroxide is increased with a corresponding increase in efficacy. The combined therapeutic efficacy of benzoyl peroxide and salicylic acid is considerably greater than the effect of each agent alone.

Salicylic acid has been suggested for use in combination with tars or mercury compounds in the treatment of psoriasis to enhance the penetration of these drugs. However, there has been no suggestion in the prior art that this would increase the antibacterial effect of benzoyl peroxide in the treatment of acne vulgaris.

It has been suggested in the prior art that the benzoyl peroxide is an effective keratolytic and antibacterial agent in the treatment of acne. In this connection, attention is directed to U.S. Pat. No. 3,535,422. This patent also suggests that the combination of precipitates sulfur and benzoyl peroxide produces greater keratolysis than either substance alone.

Although sulfur is widely regarded as keratolytic and antimicrobial, it has repeatedly been found that it enhances neither the comedolytic nor antibacterial actions of benzoyl peroxide. It has been reported that it actually encourages the formation of comedones. In a like fashion, 5% resorcinol in association with benzoyl peroxide has also been evaluated and no enhancement of therapeutic activity was evident.

The concentration of benzoyl peroxide and salicylic acid as employed in this invention is important. It has been found, for example, that 2.5% salicylic acid used in conjunction with 5% peroxide was scarcely better than benzoyl peroxide alone in the treatment of acne vulgaris. On the other hand, 10% salicylic acid with 5% benzoyl peroxide caused excessive redness and peeling in about one third of subjects treated and therefore, is of little, if any, value in this connection.

The level of salicylic acid, in accordance with this invention, will generally be in the range of from about 3% to about 7% by weight based on the total weight of the composition; whereas, benzoyl peroxide will ordinarily be employed at concentrations in the range of from about 3% to about 20% on the same basis. Optimum results are obtained when both the salicylic acid and the benzoyl peroxide are each used at a level of about 5% by weight based on the total weight of the composition.

The active ingredients employed in this invention may be applied from a variety of vehicles. In a typical sequential treatment, the salicylic acid is applied, for example as a 5% solution in a hydroalcoholic vehicle (e.g. 75% ethanol/25% water). This is followed by treatment with benzoyl peroxide applied, for example, as 5% benzoyl peroxide gel. In this procedure, the solution of salicylic acid applied to the acne lesions is permitted to dry on the skin and the 5% benzoyl peroxide gel is then immediately applied.

In another form of this invention, the salicylic acid and the benzoyl peroxide are applied simultaneously in the same vehicle, e.g. as a gel vehicle. These gels will ordinarily be aqueous gels containing gelling or thickening agents. As examples of such gelling or thickening agents, mention may be made of such materials as Veegum (magnesium aluminum silicate), sodium CMC, hydroxypropyl cellulose (e.g. Klucel HF), hydroxyethyl cellulose (Natrosol 250 HHR), hydroxypropyl methyl cellulose (Methocel A 4M); Carbopol 941 (neutralized with diisopropanolamine), etc. water dispersible starches (Nucol 4227) and mixtures thereof. The quantity of gelling or thickening agent that may be employed may vary somewhat. Ordinarily, it is comprised of about 0.1% to 5.0% by weight based on the total weight of the composition.

Although gel products of varying degrees of stability and viscosity may be prepared using any of the gelling agents suggested above, it has been a problem to develop a gel product that has a commercially acceptable stability, consistency and viscosity. A number of gelling agents were tried in an effort to prepare a commercially acceptable product. One was rejected because there resulted a destruction of the gel consistency and a separation of the suspended active ingredients. Another was rejected because it gave a thick lumpy mass which could not be dispersed even after considerable mixing. Still another, although it initially gave a satisfactory product, after several hours the viscosity dropped precipitously and this could not be considered commercially acceptable. In other instances, while the gelling agent selected provided a stable gel, it did not give a product having a commercially acceptable viscosity or smoothness.

Especially stable gel products of the present invention having the commercially requisite viscosity and texture are obtained by employing a mixture of a magnesium aluminum silicate (e.g. Veegum K) with hydroxypropyl methyl cellulose (Methocel) as the gelling agent. Although the quantities of these agents may also vary somewhat in the preferred form of this invention, the magnesium aluminum silicate will comprise from about 0.5 to 3.0% by weight based on the total weight of the composition; optimum results being obtained when the level of this material is at about 2.0% by weight. With regard to the Methocel component of the gelling agent, this may also vary. Good results are obtained with levels of Methocel in the range of from about 0.5% to 2.5% by weight based on the total weight of the composition; the best results being obtained when this is at a level of about 1.25% by weight. In any event, the combined total of magnesium aluminum silicate and Methocel will not exceed about 5% by weight based on the total weight of the composition.

It has also been found that the texture, appearance as well as the chemical stability of the gel compositions of this invention, including those that contain both salicylic acid and benzoyl peroxide (e.g. see Example 2A below) may be enhanced by incorporating therein a "Cold Process Starch", i.e. a water soluble starch. Products of this character that are especially suited for the present purposes are sold under the tradename NUCOL (e.g. NUCOL231 NUCOL 326 and particularly NUCOL 4227). These starch products may be present in the gel compositions of this invention in various quantities. However, generally it will be present in the range of from about 0.5% to about 2.0% by weight based on the total weight of the composition and preferably about 1.0%.

In general, benzoyl peroxide is chemically stable in the freshly prepared gel compositions encompassed in the present invention. However, when benzoyl peroxide is combined with salicylic acid in a gel composition that also contains laureth-4, this seems to affect the shelf-life of the product insofar as benzoyl peroxide is concerned. Cold process starches (e.g. Nucol 4227) aid in enhancing the physical stability of products of this character (e.g. the composition of Example 2A) and may also play a role in enhancing their chemical stability. This is illustrated in the chemical stability study summarized below. In this study, the various products were stored for the number of months indicated in column 1 at room temperature; 35° C. and 45° C. unless otherwise specified.

| Months | Benzoyl Peroxide Content % of Initial Assay | | |
|---|---|---|---|
| | Room Temperature | 35° C. | 45° C. |
| A. Benzoyl Peroxide 5% & Salicylic Acid 5% Gel (Example 2A) | | | |
| Zero | 100.0 | — | — |
| 1 | 99.5 | (100.4) | 98.2 |
| 2 | — | 94.7 | 92.9 |
| 4 | (100.2)[2] | (99.8) | — |
| B. Benzoyl Peroxide 5% & Salicylic Acid 5% Gel (Example 2) | | | |
| Zero | (100.0) | — | — |
| 1 | — | (84.9[1]) | — |
| 5 | (77.0) | — | — |
| C. Benzoyl Peroxide 5% Gel (Example 1, Composition B) | | | |
| Zero | 100.0 | — | — |
| 1 | — | 99.6 | 92.2 |
| 2 | 100.9 | 97.5 | 85.9[1] |
| 3 | 99.2 | 96.7 | — |

[1]Stability study discontinued at specified temperature since benzoyl peroxide content <90%
[2]( ) values in parenthesis are for product in glass containers. All other values are for product in 1½ oz. plastic tubes (white Hd P/E)

Product A and C at room temperature exhibit no instability while Product B yields substantial (i.e. greater than 20%) loss in potency at 5 months. At elevated temperatures (35° C. and 45° C.) Product A yields good stability. Product B at 35° C. exhibits very poor stability with over 15% loss of potency at 1 month. Product C yields some instability at 45° C. while at 35° C. the stability is relatively good. Overall, the stability of Product A is far superior to Product B while being similar to Product C.

Salicylic acid and benzoyl peroxide are each sparingly soluble in water. As an optional feature, to facilitate the preparation of the aqueous gel composition and yield cleansing properties to the finished product, it is sometimes useful to employ a surface active agent. A variety of surface active agents may be emloyed for this purpose. Among these, mention may be made of such materials as laureth-4, sodium lauryl sulfate, dioctyl sodium sulfosuccinate, sodium laureth sulfate, sodium sulfoacetate. The quantity of surface active agent employed can also vary. Ordinarily, this will be in the range of from about 2.0% to 6.0% by weight based on the total weight of the composition.

If a surface active agent is employed, laureth-4 is a typical choice. Laureth-4 is the CTFA name for the ethoxylated ether of lauryl alcohol having the formula $CH_3(CH_2)_{10}CH_2(OCH_2CH_2)_nOH$ wherein n has an average value of 4. Laureth-4 may be used in the present composition in the range of from about 3.0% to 6.0% by weight based on the total weight of the composition. Optionally, this is present at a level of about 6.00% by weight.

Another surface active agent which may be employed is dioctyl sodium sulfosuccinate, the CTFA name for the sodium salt of the diester of an octyl alcohol and sulfosuccinic acid which conforms to the formula:

$$CH_3(CH_2)_3-\underset{\underset{CH_2CH_3}{|}}{CH}-CH_2-O-\underset{\underset{\underset{\underset{CH_3(CH_2)_3-\underset{\underset{CH_2CH_3}{|}}{CH}-CH_2-O-\underset{\|}{\overset{\|}{C}}}{|}}{CH_2}}{HCSO_3NA}}{\overset{\overset{O}{\|}}{C}}$$

Dioctyl sodium sulfosuccinate may be used in the present composition in the range from about 0.5% to 3.0% by weight based on the total weight of the composition. Optionally, this is present at a level of about 1.0% by weight.

Another surface active agent which may be employed is sodium laureth sulfate, the CTFA name for the sodium salt of sulfated ethoxylated lauryl alcohol that conforms generally to the formula: $CH_3(CH_2)_{10}CH_2(OCH_2CH_2)_nOSO_3Na$ wherein n averages between 1 and 4.

Sodium laureth sulfate may be used in the present composition in the range from 3.0% to 6.0% by weight based on the total weight of the composition. Optionally, this is present at a level of about 4.0%.

Another surface active agent which may be employed is sodium lauryl sulfoacetate, the CTFA name for the organic salt that conforms generally to the formula:

$$CH_3(CH_2)_{10}CH_2OSO_2CH_2COO^-Na^+$$

Sodium lauryl sulfoacetate may be used in the present composition in the range from about 1.0% to 3.0% by weight based on the total weight of the composition. Optionally, this is present at a level of about 2.0% by weight.

However, under some circumstances, it is preferable to eliminate the surface active agent all together. Effective and stable gel preparations containing benzoyl peroxide and salicylic acid at the required levels have been prepared without using any surface active agent.

Other ingredients commonly contained in aqueous gel compositions may also be contained in the compositions of this invention providing they do not effect the stability of the present composition. Typical among these are the metal sequestering or chelating agents such as disodium EDTA (i.e. disodium ethylenediamine tetraacetic acid) to prevent product discoloration due to salicylic acid and metals interaction.

As indicated above, the procedures for treating acne in accordance with the present invention, involve a sequential or simultaneous application of the active ingredients. In both instances, the composition or compositions containing the actives are applied liberally twice a day until the lesions are cleared up. To control the condition, the compositions are then applied in the same fashion; once a day as long as it is thought necessary.

The following Examples are given to further illustrate the present invention. It is to be understood, however, that the invention is not limited to these examples.

EXAMPLE 1

|  | % by Wt. |
|---|---|
| Composition A |  |
| Solution |  |
| Salicylic acid | 5 |
| Ethanol | 75 |
| Water to | 100 |
| Composition B |  |
| Aqueous Gel |  |
| Benzoyl peroxide (actives) | 5.0 |
| Laureth-4 | 6.0 |
| Disodium EDTA | 0.1 |
| *Carbopol 940 | 0.5 |
| Diisopropanolamine | 0.6 |
| Water to | 100.0 |

*Carbopol 940 (CAS number DM 9007-17-4) See also U.S. Pat. Nos. 3,133,865 and 2,798,053

The composition of this Example i.e. Compositions A and B are intended for use in a sequential fashion. Each of the compositions is placed in its own dispensing container. For convenience of administration, one of each of these containers is packaged together in the same carton.

EXAMPLE 2

| Aqueous Gel |  |
|---|---|
|  | % by Wt. |
| *Veegum K | 2.00 |
| Methocel A 4M | 1.25 |
| Disodium EDTA | 0.10 |
| **Laureth-4 | 6.00 |
| Salicylic acid | 5.00 |
| Benzoyl peroxide |  |
| (approx. 70% active) | 7.79 |
| Water to | 100.00 |

*Magnesium aluminum silicate (CAS number 1327-43-1)
**$CH_3(CH_2)_{10}CH_2(OCH_2CH_2)_nOH$ wherein n has an average value of 4.

The composition of this Example is used in accordance with the present invention to simultaneously apply the salicylic acid and benzoyl peroxide.

EXAMPLE 2A

| Aqueous Gel |  |
|---|---|
|  | % by Wt. |
| Salicylic acid | 5.00 |
| Benzoyl peroxide |  |
| (approx. 70% active) | 7.14 |
| Veegum K | 2.00 |
| *Methocel A 4M | 1.25 |
| **Nucol 4227 | 1.00 |
| Disodium EDTA | .10 |
| Water to | 100.00 |

*Hydroxypropyl methyl cellulose (CAS number PM 9004-65-3)
**Cold Process Starch (modified)

The composition of this Example is also a convenient form for simultaneously applying salicylic acid and benzoyl peroxide.

EXAMPLE 3

Benzoyl Peroxide/Salicylic Acid Sequential Application in the Treatment of Acne Vulgaris Method:

Three treatments were compared in three groups of 50 adolescents with moderate acne vulgaris. The subjects had numerous open and closed comedones with a variable quantity of papules and pustules. The agents were applied twice daily for 8 weeks; the effect of treatment was assessed globally according to a widely used conventional schema:

poor = less than 25% improvement or worse
fair = 26% to 50% improvement
good = 51% to 75% improvement
excellent = greater than 75% to clear The treatments were: (1) 5% salicylic acid in 75% aqueous ethanol (Composition A, Example 1); (2) 5% benzoyl peroxide gel (Composition B, Example 1); (3) 5% salicylic acid (Composition A, Example 1) followed immediately by 5% benzoyl peroxide gel (Composition B, Example 1).

Results and Conclusions

The data are summarized in Table I below.

Benzoyl peroxide alone was somewhat superior to salicylic acid alone. Both were moderately effective. The sequence of salicylic acid and benzoyl peroxide was clearly superior to either agent alone. The response was also swifter. The latter is important to maintain patient compliance. Papulo-pustules in particular regressed more rapidly with the combination. The drying effect was also greater and this was perceived as desirable in overcoming oiliness.

All three treatments were well tolerated though temporary redness was more frequent with the combination. No subject dropped out of the study or thought the treatments too severe.

TABLE I
COMPARATIVE EFFICACY IN ACNE

|  | Excellent | Good | Fair | Poor |
|---|---|---|---|---|
| Salicyclic acid | 3% | 39% | 44% | 14% |
| Benzoyl peroxide | 8% | 46% | 39% | 7% |
| Salicylic acid plus benzoyl peroxide | 14% | 61% | 23% | 2% |

As pointed out previously, one of the features in the pathology of acne vulgaris is the formation of comedones. Any therapy that has a comedolytic effect should be beneficial in the treatment of this condition. The following Example demonstrates the comedolytic effect of a therapy that utilizes salicylic acid and benzoyl peroxide and further demonstrates that it is more effective for this purpose than the use of either alone.

EXAMPLE 4

Comedolytic Effect in Rabbit Ears

Method

Comedones were induced in both external ear canals of albino rabbits by the daily application for two weeks of 5% crude coal tar ointment.

The test agents were then applied once daily for two weeks to opposite sides. A group of five rabbits was used for each test. The tissue was biopsied and horizontally sectioned. The size of the comedones (follicular hyperkeratosis) was estimated under the microscope according to the following scale:

0 = none
1 = slight comedones
2 = moderate comedones
3 = large comedones

The treatment groups were as follows: (1) 5% benzoyl peroxide gel (Composition B, Example 1) vs. 5% ethanolic salicylic acid (Composition A, Example 1) followed immediately by 5% benzoyl peroxide gel (Composition B, Example 1); (2) 5% ethanolic salicylic acid (Composition A, Example 1) vs. 5% ethanolic salicylic acid (Composition A, Example 1) followed immediately by 5% benzoyl peroxide gel (Composition B, Example 1).

Results

The results are summarized in Tables II and III below. In both comparisons, the comedones were unequivocally smaller on the combination side. It can be seen that salicylic acid alone is more comedolytic than benzoyl peroxide.

TABLE II

| | 5% Benzoyl Peroxide vs. Sequential 5% Salicylic Acid and 5% Benzoyl Peroxide | |
|---|---|---|
| Rabbit No. | 5% Benzoyl Peroxide | Combination |
| 1 | 2 | 1 |
| 2 | 2 | 1 |
| 3 | 1 | 0 |
| 4 | 3 | 1 |
| 5 | 2 | 0 |
| means: | 2.0 | 0.6 |

TABLE III

| | 5% Salicylic Acid vs. Sequential 5% Salicylic Acid and 5% Benzoyl Peroxide | |
|---|---|---|
| Rabbit No. | 5% Salicylic Acid | Combination |
| 1 | 1 | 0 |
| 2 | 1 | 1 |
| 3 | 2 | 1 |
| 4 | 2 | 1 |
| 5 | 1 | 0 |
| mean: | 1.4 | 0.6 |

As also indicated above, another feature of the pathology of acne vulgaris is the inflammation that results from the rupture of comedones. The acne bacillus, *Propionibacterium acnes,* plays an important causal role first in contributing to the formation of comedones and then by producing toxic products that cause their rupture. Any agent which reduces the level of these organisms within the follicles should have a beneficial effect in the treatment of acne. The following Example shows that the combination of salicylic acid and benzoyl peroxide greatly reduces the quantity of *Propionibacterium acnes* on the skin. Five percent benzoyl peroxide alone is a highly effective agent in reducing the density of *Propionibacterium acnes,* being more than 95% effective. It would hardly be expected that the combination of salicylic acid and benzoyl peroxide would be superior to benzoyl peroxide alone. The combination would have to be at least as effective as benzoyl peroxide alone in reducing *Propionibacterium acnes.* This is in fact the case as is demonstrated in Example 5 below (compare Tables IV and V). However, although benzoyl peroxide alone is equivalent to the combination as as antibacterial agent, this is only one aspect for measuring the effectiveness of these materials in the treatment of acne vulgaris. As already pointed out above by the least two other parameters, that are important in the treatment of acne vulgaris, the combination of salicylic acid and benzoyl peroxide were found to be superior to either salicylic acid or benzoyl peroxide alone.

EXAMPLE 5

Comparison of Anti-microbial Effect of 5% Benzoyl Peroxide alone and 5% Benzoyl Peroxide in Sequence with 5% Ethanolic Solution of Salicylic Acid

Method

Two groups of ten healthy young adult black males were studied. These were selected because of facial characteristics associated with high levels of *Propionibacterium acnes;* namely, bright follicular fluorescence under the Woods light and excessive oiliness.

The detergent scrub method was utilized to determine the density of *Propionibacterium acnes* on the cheeks. Samples were taken before and again after one and two weeks of treatment.

The first group received 5% benzoyl peroxide gel (Composition B, Example 1) to the entire face twice daily for two weeks. In the second group, 5% salicylic acid solution (Composition A, Example 1) was applied twice daily, followed immediately each time with 5% benzoyl peroxide gel (Composition B, Example 1).

It should be noted that a third group of ten subjects received 5% salicylic acid alone. There was no effect on the density of *Propionibacterium acnes;* hence the data are not given.

TABLE IV

5% Benzoyl Peroxide Gel
Density of Propionibacterium Acnes
(millions/cm$^2$)

| Subject No. | Control Pre-Treatment | Treatment Week One | Week Two |
|---|---|---|---|
| 1 | 6.5 | 5.3 | 3.9 |
| 2 | 6.3 | 3.6 | 3.5 |
| 3 | 4.4 | 2.2 | 2.0 |
| 4 | 5.6 | 4.2 | 3.7 |
| 5 | 6.2 | 2.7 | 3.0 |
| 6 | 5.5 | 4.2 | 3.6 |
| 7 | 7.0 | 4.9 | 4.5 |
| 8 | 5.4 | 3.7 | 3.2 |
| 9 | 7.1 | 4.3 | 4.0 |
| 10 | 6.3 | 5.1 | 5.3 |
| mean: | 6.03 | 4.02 | 3.67 |

TABLE V

Sequence of 5% Salicylic Acid
and 5% Benzoyl Peroxide Gel
Density of Propionibacterium Acnes
(millions/cm$^2$)

| Subject No. | Control Pre-Treatment | Treatment Week One | Week Two |
|---|---|---|---|
| 1 | 5.5 | 4.1 | 3.2 |
| 2 | 5.7 | 4.4 | 3.1 |
| 3 | 5.5 | 2.5 | 2.8 |
| 4 | 5.9 | 4.7 | 3.9 |
| 5 | 5.2 | 3.7 | 3.0 |
| 6 | 4.6 | 3.4 | 2.9 |
| 7 | 6.1 | 4.2 | 3.2 |
| 8 | 5.6 | 5.3 | 4.6 |
| 9 | 6.5 | 2.3 | 2.5 |
| 10 | 6.3 | 4.3 | 5.1 |
| mean: | 5.69 | 3.89 | 3.43 |

The following Example illustrates the utility of the simultaneous application of 5% salicylic acid and 5% benzoyl peroxide in an aqueous gel composition. In these tests, the antibacterial effect of this combination on *Propionibacterium acnes* was examined.

EXAMPLE 6

Method

The composition of Example 2A was applied twice daily for two weeks to the faces of ten healthy, young adult black males with oily skin. *Propionibacterium acnes* densities were determined before and again after one and two weeks of treatment. The results are summarized in Table VI.

Results

These show that the reduction of *Propionibacterium acnes* with the combination was rather similar to that previously obtained with application of each agent in sequence. On the average, the *Propionibacterium acnes* population was reduced by 95% and more. The mixing of these two agents in one formulation does not result in loss of the desired effect although it takes somewhat longer to reach this effect.

TABLE VI

Combination of 5% Salicylic Acid
and 5% Benzoyl Peroxide
in a Gel Product
(millions/cm$^2$)

| Subject No. | Control Pre-Treatment | Treatment Week One | Week Two |
|---|---|---|---|
| 1 | 6.3 | 4.8 | 4.6 |
| 2 | 5.5 | 4.2 | 3.5 |
| 3 | 4.8 | 3.8 | 3.2 |
| 4 | 5.9 | 5.0 | 3.7 |
| 5 | 7.0 | 4.6 | 3.6 |
| 6 | 6.4 | 5.2 | 4.3 |
| 7 | 5.2 | 4.1 | 2.4 |
| 8 | 5.7 | 5.0 | 3.6 |
| 9 | 6.1 | 4.3 | 2.5 |
| 10 | 5.5 | 3.6 | 3.0 |
| mean: | 5.8 | 4.5 | 3.4 |

What is claimed is:

1. A method for treating acne vulgaris comprising applying to the skin of a subject having this condition a therapeutically effective of salicylic acid and benzoyl peroxide for a period of time sufficient to alleviate symptoms of said acne condition, said salicylic acid being applied at a concentration in the range of from about 3% to 7% by weight and said benzoyl peroxide being applied at a concentration of about 3% to 20% by weight; said percentages being expressed on a weight basis based on the total weight of compositions containing said benzoyl peroxide or salicylic acid or the combination of benzoyl peroxide and salicylic acid.

2. A method according to claim 1 in which the concentration of the salicylic acid is about 5% by weight and the concentration of the benzoyl peroxide is about 5% by weight.

3. A method according to claim 2 in which the salicylic acid and benzoyl peroxide are applied sequentially.

4. A method according to claim 2 in which said salicylic acid and benzoyl peroxide are applied simultaneously.

5. A method according to claim 4 in which said salicylic acid and said benzoyl peroxide are contained in the same pharmaceutically accpetable vehicle.

6. A topical therapeutic composition comprising a pharmaceutically acceptable vehicle containing by weight, based on the total weight of said composition, from about 3% to about 7% salicylic acid and about 3% to 20% benzoyl peroxide.

7. A composition according to claim 6 containing about 5% salicylic acid and 5% benzoyl peroxide.

8. A composition according to claim 7 in which said vehicle is an aqueous gel.

9. A composition according to claim 8 containing as gelling and/or thickening agents magnesium aluminum silicate and hydroxypropyl methylcellulose.

10. A composition according to claim 9 in which the magnesium aluminum silicate is present in an amount in the range of from about 0.5 to about 3.0% by weight based on the total weight of the composition and said hydroxypropyl methylcellulose is present in an amount in the range of from about 0.5 to 2.5% by weight based on the total weight of the composition; the combined amount of said magnesium aluminum silicate and said hydroxypropyl methylcellulose not exceeding about 5% by weight.

11. A composition according to claim 10 containing about 2% by weight of magnesium aluminum silicate and about 1.25% by weight of hydroxypropyl methylcellulose.

12. A composition, according to claim 10, further including an amount of a metal sequestering or chelating agent sufficient to prevent product discoloration due to salicylic acid and metals interaction.

13. A composition, according to claim 12 further including from about 0.5% to 2.0% by weight, based on the total weight of the composition, of a water soluble Cold Process Starch.

* * * * *